United States Patent [19]

Bowman

[11] Patent Number: 5,346,473
[45] Date of Patent: Sep. 13, 1994

[54] OXY-HYDROGEN PROPELLED TORPEDO FOR INTRODUCING ANGIOPLASTY GUIDE WIRE

[75] Inventor: Robert L. Bowman, Bethesda, Md.

[73] Assignee: The United States of America as represented by the Department of Health and Human Services, Washington, D.C.

[21] Appl. No.: 20,952

[22] Filed: Feb. 22, 1993

[51] Int. Cl.$^5$ .............................. A61M 37/00
[52] U.S. Cl. ..................... 604/95; 606/159; 606/170
[58] Field of Search ............ 604/95, 69, 145, 147; 606/159, 167-171, 190, 184, 178, 179, 180

[56] References Cited

U.S. PATENT DOCUMENTS

| | | | |
|---|---|---|---|
| 3,022,785 | 2/1962 | Crockford et al. | 604/145 |
| 3,308,818 | 3/1967 | Rutkowski | 604/69 |
| 3,335,722 | 8/1967 | Lowry et al. | 604/69 |
| 3,665,928 | 5/1972 | Del Guercio | 604/95 |
| 4,124,024 | 1/1978 | Schwebel et al. | 604/69 |
| 4,717,381 | 1/1988 | Papentonakos | 604/95 |
| 4,769,006 | 9/1988 | Papantonakos | 604/95 |
| 5,234,451 | 8/1993 | Osypka | 606/159 |

FOREIGN PATENT DOCUMENTS 2645009 10/1990 France ................. 604/159

*Primary Examiner*—John D. Yasko
*Assistant Examiner*—Frank Wilkens
*Attorney, Agent, or Firm*—Lowe, Price, LeBlanc & Becker

[57] ABSTRACT

A torpedo device which is attached to the end of a guide wire to provide a local driving force to the end thereof. The torpedo includes a telescopic structure having a combustion chamber therein. In operation, a combustible fuel is fed to the combustion chamber and an explosion is created by igniting the combustible fuel. Upon explosion, the torpedo expands axially to drive a projectile portion thorough an obstructed or constricted vessel lumen. Fins can be included on the exterior of the torpedo to prevent backward movement. The fins can also be used to scrape or cut an obstruction by engaging the obstruction and subsequently applying rearward movement to the torpedo.

19 Claims, 1 Drawing Sheet

OXY-HYDROGEN PROPELLED TORPEDO FOR INTRODUCING ANGIOPLASTY GUIDE WIRE

TECHNICAL FIELD

The present invention relates to wire-directed catheters. More particularly, the present invention relates to a torpedo device which provides a local driving force on the end of a guide wire.

BACKGROUND ART

A number of self-propelled catheters and at least one self-propelled baroscope have been developed which avoid problems associated with manual or forced insertion. For example, U.S. Pat. No. 4,934,786 to Krauter discloses a walking baroscope which includes an inflatable-bladder walking arrangement on the outer surface of the baroscope insertion tube.

U.S. Pat. No. 4,769,006 to Papantonakos discloses a hydrodynamically propelled pacing catheter which is constructed with a plurality of nozzle orifices for the expulsion of a pressurized fluid so that the catheter will be propelled through a patient's vascular system.

U.S. Pat. No. 4,249,536 to Vega discloses a urological catheter which includes a magneto-insert embedded within the tip that is used in cooperation with an electromagnet externally of the catheter to propel the catheter along the urethra by repulsive or attractive lines of magnetic force.

None of these prior art devices are specifically adapted for confronting and passing through obstructions or constrictions.

The passage of a guide wire through a constricted atherosclerotic plaque-filled cardiac artery is an essential first step to perform angioplastic procedures for relief of coronary artery disease symptoms. Very tight strictures often render angloplastic procedures difficult or impossible.

The device and procedure of the present invention is expected to increase the success rate of angioplastic procedures.

DISCLOSURE OF THE INVENTION

It is accordingly one object of the present invention to provide a wire-directed catheter.

Another object of the present invention is to provide an angioplasty guide wire.

It is another object of the present invention to provide a torpedo device which provides a local driving force on the end of a guide wire.

A further object of the present invention is to provide a torpedo device which can be used to scrape or shave an obstruction from the inside of an arterial or vascular lumen.

A further object of the present invention is to provide a method for passing a wire-directed catheter through a constricted or obstructed lumen.

A still further object of the present invention is to provide a method for scraping or shaving an obstruction from the inside of an arterial or vascular lumen.

According to these and further objects of the present invention which will become apparent as the description thereof is presented below, the present invention provides a wire-directed catheter which includes:

a guide wire having a distal and a proximal tip; and projectile means attached to the proximal tip of the guide wire for propelling the wire-directed catheter through a lumen.

The projectile means includes a base portion which is attached to the proximal tip of the guide wire and a projectile portion which are telescopically connected to each other so as to define a combustion chamber therebetween.

A fuel feed tube having valve means, including a pinch valve, communicates with the combustion chamber and serves as a means to supply a combustible fuel to the combustion chamber. The fuel feed tube also includes hollow metal needles having porous plugs therein which prevent flashback of the combustible fuel.

An ignition wire is provided for igniting combustible fuel supplied to the combustion chamber. The ignition wire passes through the base portion and may pass through a portion of the fuel feed tube into the combustion chamber.

A plurality of fins may be provided which extend either from an outer surface of the projectile portion or from outer surfaces of both the projectile portion and the base portion.

The tip of the guide wire can include steering means.

The present invention also provides a method of passing a wire-directed catheter through all obstructed lumen which involves:

providing a wire-directed catheter having a guide wire with a projectile means attached to a proximal tip of the guide wire for propelling the wire-directed catheter through a lumen;

positioning the projectile means at an obstruction in a lumen; and activating the projectile means so that a portion thereof is projected into or through the obstruction while the proximal tip of the guide wire remains stationary.

According to this method, the projectile means is activated once or repeatedly by causing an explosion(s) to occur therein. One-directional movement of the wire-directed catheter can be ensured by providing fins on the projectile means.

The present invention further provides a method of clearing an obstruction from a lumen which involves:

providing a wire-directed catheter having a guide wire with a projectile means attached to a proximal tip of the guide wire for propelling the wire-directed catheter through a lumen;

positioning the projectile means at the obstruction in the lumen;

activating the projectile means so that a portion thereof is projected into or through the obstruction while the proximal tip of the guide wire remains stationary; and retracting the portion of the projectile means from the obstruction.

According to this method the obstruction is engaged by fins provided on the projectile means.

BRIEF DESCRIPTION OF THE DRAWINGS

The present invention will be described with reference to the annexed drawings which are given by way of non-limiting examples only, in which.

BEST MODE FOR CARRYING OUT THE INVENTION

The present invention is directed to a projectile means or small torpedo device which is mounted on the tip of a guide wire and used to propel the wire through a constricted or obstructed lumen. When the guide wire encounters an obstruction which it cannot clear or pass through by exerting pressure on the distal end thereof according to conventional procedures, the torpedo mounted on the tip of the guide wire can be actuated to drive the torpedo and pull the guide wire through the obstruction.

The present invention was developed to be particularly useful in conjunction with angioplasty procedures. In this regard, the torpedo can be attached to the tip of an angioplasty wire and used to guide wire-directed catheters through constricted cardiac arteries. Although particularly useful for angioplastic procedures, it is to be understood that the torpedo device of the present invention could be used in conjunction with any type of wire-directed catheter for guiding such catheters through obstructions in various arterial or vascular lumens.

Because guide wires are required to be very flexible, it is often difficult or impossible to force such guide wires through obstructions in lumens or even to take up slack as the guide wires are being inserted without some form of local driving force. The present invention overcomes such problems by providing a local driving force on the proximal end or insertion tip of the guide wire.

According to the present invention, a projectile means, or "torpedo", is attached to the tip of a guide wire. The torpedo provides a local driving force when activated as described below. In addition, according to one embodiment of the present invention, the tip of the torpedo can be equipped with external fins or blades which function as cutting blades when the tip of the torpedo is retracted or oscillated within a constriction. In such an operation, the torpedo can be used to scrape or shave an obstruction from the inside of an arterial or vascular vessel.

When activated, a small explosion takes place inside the torpedo. The force of the small explosion causes the structure of the torpedo to expand in the axial direction so as to push forward through an encountered constriction or obstruction. The explosion is created by igniting combustible gases which are controllably fed into a combustion chamber provided in the interior of the torpedo structure. After an explosion, the combustion product gases condense, thereby allowing the torpedo to collapse or retract.

Figure 1:
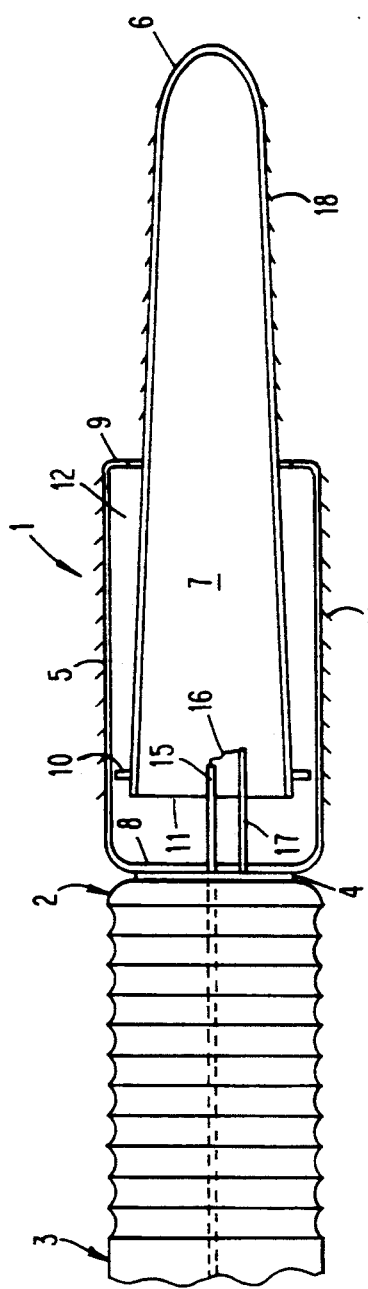
FIG. 1 is a schematic cross-sectional view of the torpedo device according to one embodiment of the present invention in which the torpedo is in a collapsed or retracted state.

FIG. 1 is a schematic cross-sectional view of the device according to one embodiment of the present invention in which the torpedo device is in a collapsed or retracted state. In FIG. 1 the torpedo 1 is depicted as being attached to a proximal end or tip 2 of a guide wire 3. The tip 2 of the guide wire 3 is preferably a flexible tip which can include conventional steering means (not shown) for directing the guide wire 3 through a lumen of other remote situs in a known manner. The torpedo 1 is attached to the tip 2 of the guide wire 3 by soldering, welding, cementing, or other suitable means. According to a preferred embodiment, the torpedo 1 is attached to the tip 2 of the guide wire 3 by a silver solder portion 4.

The torpedo 1 includes a rear base portion 5 and a forward projectile portion 6 which define a combustion chamber 7 therebetween. The base portion 5 includes a closed end 8 which is attached to the tip 2 of the guide wire 3 as depicted in FIG. 1.

The projectile portion 6 is telescopically movable with respect to the base portion 5. In this regard, the base portion 5 and the projectile portion 6 each have complementary axial cross-sectional shapes, e.g., circular, with the circumferential perimeter of the projectile portion 6 being slightly smaller that the inside diameter of the base portion 5.

Figure 2:
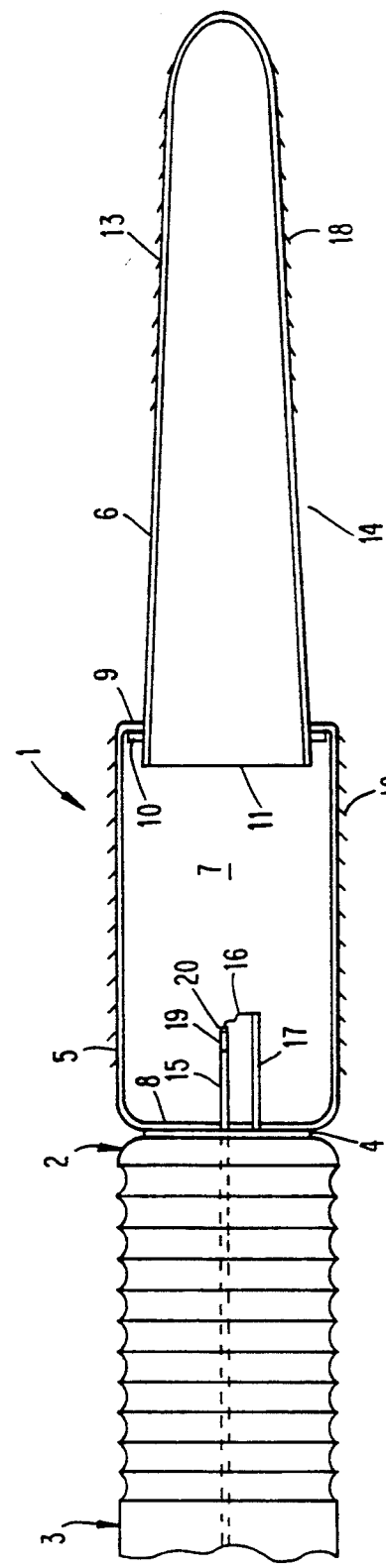
FIG. 2 is a schematic cross-sectional view of the torpedo device according to one embodiment of the present invention in which the torpedo is in an expanded or extended state.

As shown, the projectile portion 6 is positioned within the base portion 5 in such a manner so that the projectile portion can telescopically move with respect to the base portion 5 between a collapsed position as shown in FIG. 1 and an expanded position as shown in FIG. 2. In an alternative embodiment, the base portion 5 can be positioned within the projectile portion 6. In this alternative embodiment it to be understood that the arrangement of the abutment members discussed below and the relative diameters of the base and projectile portion are reversed.

Abutment members 9 and 10 are respectfully provided on the base portion 5 and the projectile portion 6 to limit the forward movement of the projectile portion 6. As depicted, the abutment member(s) 9 of the base member 5 project radially inward from the open end of the base portion 5, whereas the abutment member(s) 10 of the projectile portion 6 extend radially outward from the distal or open end 11 of the projectile portion 6.

In operation, when the torpedo is activated, as discussed below, the projectile portion 6 moves forward within the base portion 5 until the abutment members 9 and 10 contact each other and stop the forward movement of the projectile portion 6. The abutment members 9 and 10 preferable extend continuously along the entire periphery or circumference of the base portion 5 and projectile portion 6 from which they extend.

In an alternative embodiment, either one of the abutment member(s) 9 or 10 can comprise a plurality of discrete projections which are symmetrically spaced about the periphery or circumference of the base portion 5 or projectile portion 6 from which they extend. It is preferred that the abutment member(s) 9 on the base portion 5 extends continuously along the entire periphery or circumference thereof so as to provide a seal between the base portion 5 and projectile portion 6 which prevents liquids and other materials from passing therebetween and entering the interior of the torpedo. In this embodiment, by providing the abutment member(s) 10 as discrete elements, venting is provided in the annular space 12 defined between the base portion 5 and projectile portion 6 and abutment members 9 and 10. In order to further ensure a seal between the base portion 5 and the projectile portion 6, a small resilient seal member (not shown) can be attached to abutment member 9.

The abutment members 9 and 10 can be welded or soldered to the respective base and projectile portion. Otherwise, the abutment members 9 and 10 can be formed integrally with the respective base or projectile portion by conventional fabrication methods.

The forward-most end 13 of the projection portion 6 tapers to a smooth conical shape as shown. The opposite end 14 of the projectile portion 6 which slides within the base portion 5 is substantially cylindrical.

A fuel feed tube 15 extends through the rear end 8 of the base portion 5 and terminates a short distance into the base portion 5 as shown. The fuel feed tube 15 extends in an opposite direction through or along side of the guide wire 3 to terminate at a distal end (not shown).

An ignition wire 16 is provided in the combustion chamber 7 and used to activate an explosion in the torpedo as discussed below. The ignition wire 16 passes through the base portion 5 and is supported away from the interior walls of projectile portion 6 and base portion 5 by a support 17. In a preferred embodiment, the ignition wire 16 enters the base portion 5 through the fuel feed tube 15 as shown. In alternative embodiments, the ignition wire 16 can extend through the rear end 8 of the base portion 5 without passing through the fuel feed tube 15. In the embodiment depicted in the figures, the ignition wire 16 can pass through substantially the entire length of the fuel feed tube 15 which is attached at a distal end to a source of fuel as discussed hereafter. In other embodiments, the ignition wire 16 can be secured along the exterior side of the fuel feed tube 15. The only restriction on the ignition wire, which will become readily apparent, is that the ignition wire 16 (and fuel feed tube) have a sufficient length so that the torpedo can be positioned remotely in a lumen.

The torpedo can be made of any material which is suitably strong for withstanding the explosion created therein. Moreover, the material of the torpedo should be bio-compatible. Preferable materials from which the torpedo can be made include white gold and platinum, iridium, titanium or alloys thereof or the like. The diameter of the torpedo should be equal or to slightly larger than the diameter of the guide wire, which is of a conventional design, having a diameter within a range known to those skilled in the art.

One-way blades or fins 18 can be attached or machined to the surface of the projectile portion 6 and/or base portion 5. As shown, these one-way blades or fins extend at an acute angle from the surface of the respective base or projectile portion. The blades or fins 18 provide one of two functions. First, one-way blades or fins 18 on both the base portion 5 and projectile portion 6 prevent rearward movement of the torpedo by engaging the inner surface of a constricted or obstructed lumen and thus encourage forward driving motion of the device. In another embodiment, one-way blades or fins 18 on the base or projectile portion can be used to scrape or shave an obstruction from the inside of an arterial or vascular lumen when the guide wire base and projectile portion are manually pulled backward or when the projectile portion is oscillated back and forth in the axial direction.

During the course of the present invention, the inventor has discovered a unique way of fabricating the blades or fins 18 on the base and projectile portions. In this regard, the end of a quill from a Canadian porcupine, which has a plurality of fine barb structures is used in a type of lost wax molding or casting process. Specifically, the end of a quill from a Canadian porcupine is embedded in a mold material such as Cristobalite ® to form a mold. Thereafter, the quill is removed from the mold by pyrolysis. The resulting mold can be used to cast the base and projectile portions of the present invention. When molded and cast, the barb structures on the quill produce the blades or fins of the present invention.

In an alternative embodiment, it has been determined that a sea urchin spine can be used in a type of lost wax molding or casting process. However, since the barb structures on a sea urchin spine project in a reverse direction than those of a porcupine quill, the final mold must be inverted. Accordingly, an intermediate mold of a silicon rubber material or similar resilient material is made and turned inside out.

In operation, a combustible fuel such as gaseous mixture of oxygen and hydrogen is fed into the torpedo 1 through the fuel feed tube 15. Thereafter, the ignition wire 16 ignites the fuel within the torpedo, e.g., by creating an electrical spark. Such a spark can be created by including a double wire in the ignition wire 16 with a spark gap in the end thereof or by providing a gap between the end of the ignition wire 16 and a conductive inner surface or structure (such as the support 17) in the combustion chamber 7 and passing an electric potential through the ignition wire 16.

In a preferred embodiment, the electrical spark is generated using a piezoelectric material. The piezoelectric material is provided with electrodes on opposite sides thereof and the electrodes are connected to the ignition wire. To create a spark, a load, i.e. pressure, is applied to the piezoelectric material. The load causes the piezoelectric material to act like a charged condenser, sending a single, high voltage pulse through the ignition wire so that a spark is generated in the combustion chamber.

As the combustible gases expand during the resulting explosion, the torpedo 1 expands from the collapsed to the expanded state as shown in the figures. After being expanded, the torpedo can be collapsed by merely pushing on the distal end of the guide wire. In addition, condensation of the product gases of the explosion (i.e., steam) can assist retraction of the torpedo structure. The minute quantity of water produced by condensing steam after an explosion can be allowed to leak out of the torpedo through a small vent in order to permit a subsequent explosion within a few seconds, and may be used to control or determine the firing frequency.

According to a preferred embodiment of the present invention, the combustion gases include only hydrogen and oxygen which are produced by an electrolysis cell in which water is electrolytically converted to hydrogen and oxygen. The use of such an electrolysis cell ensures that the combustion product is only steam (water) since the hydrogen and oxygen are produced by the electrolysis cell and supplied to the combustion chamber in proper stoichiometric proportions.

Flashback of an explosion through fuel feed tube 15 during ignition and continued combustion after firing the torpedo can be prevented by delivering the combustible fuel gases through small metal needles with porous sintered metal plugs. Such small metal needles 19 having porous sintered metal plugs therein can be inserted into the fuel feed tube 15 in or near the proximal end 20 as depicted in FIG. 2.

A simple interruption of the flow of combustible fuel can be used to extinguish any flame which would continue to burn after the combustible gases are ignited. Moreover, a momentary back flow of the fuel feed can be used to turn the gas off and render the device ready to fire a subsequent shot.

Figure 3:
FIG. 3 is a schematic drawing of a valve assembly used to supply a combustible fuel to the torpedo according to one embodiment of the present invention.

FIG. 3 is a schematic drawing of a valve assembly used to supply a combustible fuel to the torpedo according to one embodiment of the present invention. As depicted in FIG. 3 a solenoid operated pinch clamp or pinch valve 21 is provided in the fuel feed tube 15 down stream of a stop valve 22 (the arrow in FIG. 3 points toward the torpedo 1 and indicates the direction of flow of the combustible fuel). The fuel feed tube 15 is made of a pliable gas tight plastic or rubber material such as Supramid ® or Saran ®, PDVF, or the like. The pinch valve 21 is activated to stop the fuel flow. Next, the stop valve 22 is closed. After the stop valve 22 is closed, opening the pinch valve 21 creates a small, momentary back flow in the downstream portion of the fuel line. Subsequently, opening the stop valve 22 causes continuation of the fuel flow. The momentary back flow in the fuel line caused by releasing the pinch valve 21 while keeping the step valve 22 closed assists in preventing flashback of an explosion through fuel feed tube 15 during ignition and continued combustion after firing the torpedo. In other embodiments, the stop value 22 and pinch valve 21 could be substituted with other, functionally equivalent valves.

Since the combustion product of the fuel after explosion is only steam which immediately condenses to admit new gases into the torpedo, multiple explosions can be produce inside the torpedo within a relatively short period of time.

Although the present invention has been described with reference to particular means, materials and embodiments, from the foregoing description, one skilled in the art can easily ascertain the essential characteristics of the present invention and various changes and modifications may be made to adapt the various uses and characteristics without departing from the spirit and scope of the present invention as described by the claims which follow.

I claim:

1. A wire-directed catheter which comprises:
   a guide wire having a distal end and a proximal tip; and
   ramming means attached to the proximal tip of the guide wire for propelling said wire-directed catheter through a lumen, said ramming means comprising a hollow base portion and a hollow ram portion which are telescopically connected to each other so as to define a hollow combustion chamber therebetween.

2. A wire-directed catheter according to claim 1 wherein said base portion is fastened to the proximal tip of said guide wire.

3. A wire-directed catheter according to claim 1, wherein said ramming means further comprises means for supplying a combustible fuel to said combustion chamber.

4. A wire-directed catheter according to claim 3, wherein said means for supplying combustible fuel comprises a fuel feed tube which communicates with said combustion chamber.

5. A wire-directed catheter according to claim 3, wherein said ramming means further comprises means for igniting combustible fuel supplied to said combustion chamber.

6. A wire-directed catheter according to claim 5, wherein said means for igniting comprises an ignition wire which passes through said base portion.

7. A wire-directed catheter according to claim 6, wherein said means for supplying combustible fuel comprises a fuel feed tube which communicates with said combustion chamber and said ignition wire passes through a portion of said fuel feed tube into said combustion chamber.

8. A wire-directed catheter according to claim 1, wherein said ram portion includes a plurality of fins extending from an outer surface thereof.

9. A wire-directed catheter according to claim 8, wherein said base portion includes a plurality of fins extending from an outer surface thereof.

10. A wire-directed catheter according to claim 1, wherein said proximal tip of said guide wire comprises a steerable tip.

11. A wire-directed catheter according to claim 4, wherein a distal portion of said fuel feed tube includes valve means, including a pinch valve.

12. A wire-directed catheter according to claim 11, wherein a flashback arresting means is provided in said fuel feed tube.

13. A wire-directed catheter according to claim 12, wherein said flashback arresting means comprises hollow metal needles with porous plugs therein.

14. A method of passing a wire-directed catheter through an obstructed lumen which comprises:
    providing a wire-directed catheter having a guide wire with a ramming means attached to a proximal tip of the guide wire for propelling said wire-directed catheter through a lumen, said ramming means comprising a hollow base portion and a hollow ram portion which are telescopically connected to each other so as to define a hollow chamber therebetween;
    positioning said ramming means at an obstruction in a lumen; and
    activating said ramming means so that a portion thereof is projected into or through said obstruction while said proximal tip of said guide wire remains stationary.

15. A method of passing a wire-directed catheter through an obstructed lumen according to claim 14, wherein said ramming means is activated by causing an explosion to occur within said hollow chamber.

16. A method of passing a wire-directed catheter through an obstructed lumen according to claim 15, wherein said ramming means is repeated activated multiple times.

17. A method of passing a wire-directed catheter through an obstructed lumen according to claim 14, wherein one-directional movement of said wire-directed catheter is provided by fins on said ramming means.

18. A method of clearing an obstruction from a lumen which comprises:
    providing a wire-directed catheter having a guide wire with a ramming means attached to a proximal tip of the guide wire for propelling said wire-directed catheter through a lumen, said ramming means comprising a hollow base portion and a hollow ram portion which are telescopically connected to each other so as to define a hollow chamber therebetween;
    positioning said ramming means at said obstruction in said lumen;
    activating said ramming means so that a portion thereof is projected into or through said obstruction while said proximal tip of said guide wire remains stationary; and
    retracting said portion of said ramming means from said obstruction.

19. A method of clearing an obstruction from a lumen according to claim 18, wherein said obstruction is engaged by fins provided on said ramming means.

* * * * *